United States Patent [19]

Slocum

[11] 4,416,283

[45] Nov. 22, 1983

[54] PROGRAMMING AND TELEMETRY SYSTEM FOR BIOMEDICAL IMPLANTABLE DEVICE

[75] Inventor: Chester D. Slocum, Miami, Fla.

[73] Assignee: Cordis Corporation, Miami, Fla.

[21] Appl. No.: 297,746

[22] Filed: Aug. 31, 1981

[51] Int. Cl.³ .............................................. A61N 1/36
[52] U.S. Cl. ............................................. 128/419 PG
[58] Field of Search .................. 128/419 PG, 419 PT, 128/903

[56] References Cited

U.S. PATENT DOCUMENTS 3,563,247 2/1971 Bowers ........................ 128/419 PG
4,223,679 9/1980 Schulman et al. ............ 128/419 PT
4,281,664 8/1981 Duggan ............................... 128/903

Primary Examiner—William E. Kamm
Attorney, Agent, or Firm—Kenway & Jenney

[57] ABSTRACT

A shunted coil telemetry transponder in an implant is employed as a magnetic pulse transducer for receiving externally transmitted data. Additional circuitry reproduces the pulse waveform from inductive spikes and interfaces a programming data input with an auxiliary reed switch used for the diagnostic mode.

17 Claims, 2 Drawing Figures

PROGRAMMING AND TELEMETRY SYSTEM FOR BIOMEDICAL IMPLANTABLE DEVICE

CROSS-REFERENCE TO RELATED APPLICATIONS

This application is related to the following U.S. Patent applications, assigned to the assignee of the present application, each of which is incorporated in its entirety herein:

"Implant Telemetry System," Slocum et al., U.S. Pat. application Ser. No. 153,093 filed May 27, 1980, now U.S. Pat. No. 4,361,153 issued Nov. 30, 1982;

"Implantable Externally Programmable Microprocessor-Controlled Tissue Stimulator," Lesnick, U.S. Patent application Ser. No. 196,665 filed Oct. 9, 1980;

"Interactive Programmer For Biomedical Implantable Devices," Mumford et al., U.S. Patent application Ser. No. b 281,011, filed July 6, 1981.

BACKGROUND OF THE INVENTION

The invention relates generally to electromagnetic signalling and telemetry for biomedical implantable devices.

The increasing versatility of implanted stimulators such as cardiac pacers demands more complex programming capabilities. Programming in this context means noninvasively transferring parameter value data from an external device called the programmer to an internal device implanted in the patient's body. A number systems have been successfully employed in commercially available cardiac pacers, including magnetic programming and radio frequency (RF) programming. RF programming suffers from the unavoidable inherent disadvantage of electromagnetic interference in the environment which an active cardiac pacer patient may encounter. Magnetic programming, on the other hand, relies upon the generation of a series of strong magnetic impulses which actuate a reed switch inside the pacer. Additional circuitry recreates the magnetic pulse waveform from the openings and closings of the reed switch in response to the pulsating magnetic field. The output of the reed switch circuit forms the programming input to programming data registers in the implant, as shown, for example, in U.S. Pat. No. 3,805,796 to Terry et al., assigned to the assignee of the present application.

Reed switch programming is not to be confused with so called "magnet rate, " long a standard feature of demand cardiac pacers. Cardiac pacers which stimulate only when necessary to fill in "missing beats" are called standby or demand pacers. To check the inherent fixed rate of this pacer, i.e., the rate to which the pacer will revert in the absence of spontaneous cardiac activity, the physician can place a permanent magnet over the pacer site to actuate a reed switch. The pacer circuitry is designed to respond by removing the demand feature and switching to asynchronous or fixed rate operation so that the physician can not only check the fixed rate but can determine whether the pacer still is operating above the "capture threshold" and, in certain designs, check the pacer's batteries. In pacers such as Cordis "Omnicor ®", where the same reed switch is used for this diagnostic mode or magnet rate, and for programming (i.e., selecting new parameter values), the pacer is equipped with timing circuitry to distinguish between magnetic impulses and a constant magnetic field.

Reed switches have a number of desirable attributes. Besides having little or no associated current drain in the quiescent mode, the insensitivity of reed switches protects against spurious programming. In addition, of course, it is possible to use the same sensor for the conventional diagnostic mode as well as for programming.

On the other hand, with the trend to smaller pacer enclosures, the size reduction of the tiny mechanical reed switch element further reduces the sensitivity of the reed switch and its reliability and range of operation. The reed switch is essentially a threshold device dependent upon the proximity of the source of the magnetic field. Thus, with a given magnetic pulse train, the duty cycle of the pulse reproduced by the reed switch circuit depends on the distance between the programmer and the implant. In addition, a debounce circuit is necessary.

Some types of pacers only count magnetic impulses, such as the Cordis Omnicor, Telectronics and the Microlith-P ® manufactured by Cardiac Pacemakers, Inc. of Minnesota. However, substantial duty cycle distortion is intolerable in pacer designs using pulse width modulation of magnetic impulses.

SUMMARY OF THE INVENTION

Accordingly, the general purpose of the present invention is to eliminate the dependency of implant programming on the reed swith used as a data transducer.

It has been discovered that the shunted coil telemetry transponder developed for a different purpose and disclosed in the above referenced copending application entitled "Implant Telemetry Stystem," can be pressed into service not only as a transmitter but also as a receiver. The shunted coil telemetry transponder was invented in response to the need to develop a compatible telemetry system for signalling out of the implant within the energy budget constraints imposed by battery operated cardiac pacers. This passive transmitter system is implemented by a switching circuit, controlled by an implant data input, connected across a capacitor and a thin flat coil connected electrically in parallel. An externally generated myriametric (preferably 16 kHz) frequency magnetic carrier signal is resonantly reflected by the tuned coil in the implant. The lagging phase angle of the reflected signal is modulated at extremely low power by intermittently shunting the tuned coil with the data switch to accomplish transmission of data from the implant to the programmer or other external device.

In the present invention the tuned coil in the implant is employed as a magnetic pulse transducer for receiving externally transmitted data. Additional circuitry reproduces the magnetic pulse waveform from inductive spikes which appear across the tuned coil on the edges of the magnetic pulse. The spikes are rectified and used to trigger a flip-flop arrangement which exactly duplicates the magnetic pulse waveform without duty cycle distortion. Additional circuitry interfaces the programming data input of the implant with an auxiliary reed switch used solely for the diagnostic mode. During programming the reed switch is automatically isolated from the data programming input. In the diagnostic mode, the positive control of the reed switch is retained as in conventional pacers.

BRIEF DESCRIPTION OF THE DRAWINGS

FIG. 2 is a composite waveform timing diagram of typical signals appearing in the circuit of FIG. 1 at the indicated test points.

DESCRIPTION OF THE PREFERRED EMBODIMENT

The circuit of FIG. 1 operates as both data transmitter and data receiver for a biomedical implantable device designed to be used for two-way communication in conjunction with the programming head illustrated and described in connection with FIGS. 1-4 of the above referenced copending application entitled "Implant Telemetry System" (hereinafter the "Implant Telemetry application"). As described in that application, the programming head includes a relatively substantial magnetic programming coil for transmitting data to the implant as well as a coaxial triple coil assembly for activating the implanted transponder comprising the tuned coil combination L1 and C1 of FIG. 1 of the present application. When activated, the transponder in the implant can transmit data out to the external programmer.

Figure 1:
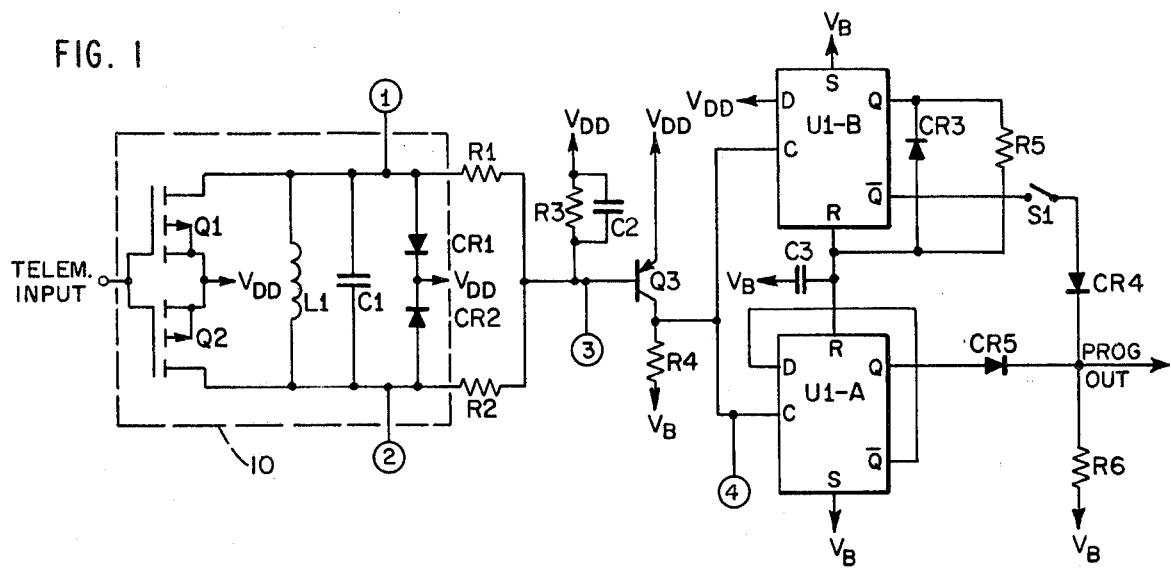

A portion of the circuit of FIG. 1 designated 10 corresponds to the V-MOS circuit of FIG. 18 of the Implant Telemetry application. D-MOS FETs can also be used. When the myriametric transmitter system is in operation to allow data transmission from the implant, the binary data telemetry input to complementary transistors Q1 and Q2 shunts the tuned coil, correspondingly changing the phase of the reflected signal detected by the triple coil assembly in the external programmer (not shown).

Figure 2:
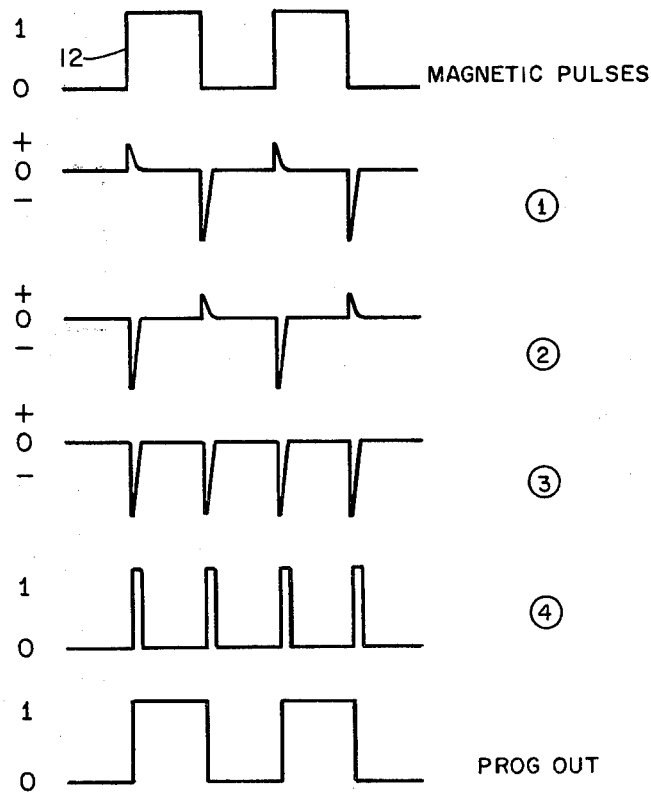
FIG. 2 is an electrical schematic of the circuit according to the invention.

The remainder of the implanted circuitry of FIG. 1 adapts the tuned coil and diode network associated with circuit 10 as a receiver for magnetic impulses. Magnetic programming pulses are produced by intermittently passing current through the magnetic programming coil in the external programming head (not shown). The resultant flux change, graphed in ideal form in the first line of FIG. 2, is sensed by coil L1 of FIG. 1 which acts like a secondary winding. Each edge 12 of the magnetic pulses produces a corresponding spike at test points 1 and 2 as shown in corresponding lines of FIG. 2. Schottky diodes CR1 and CR2 clip the positive excursion. Resistors R1 and R2 sum the complementary spikes to produce the resulting waveform at test point 3. Transistor Q3 is turned on abruptly by each spike corresponding to each edge of the magnetic impulses. Resistor R3 biases transistor Q3 off during the quiescent state. Roll-off capacitor C2 in parallel with resistor R3 prevents external interference from triggering the circuit. R4 is the collector load resistance for transistor Q3.

The positive going edge of the collector of transistor Q3 clocks the dual "D" flip-flop U1. The lower flip-flop U1-A divides the input clock string by two in order to exactly reproduce the original magnetic impulse waveform with the same pulse widths. The other flip-flop U1-B performs two functions. First, if U1 is set by powering up the circuit or if an odd number of pulses has been received, U1-B provides a reset via resistor R5 and capacitor C3. Resistor R5 can be an active trim external resistor. The combination R5 and C3 is picked so that the time constant will not interfere with programming or telemetry. Diode CR3 provides a rapid discharge of capacitor C3 once flip-flop U1-B has been reset. Thus, the circuit is ready for a new transmission almost immediately.

The second function of the upper flip-flop U1-B is to remove the effect of the diagnostic mode reed switch S1 from the programming input. Since the reed switch S1 closes during the magnetic input from the electromagnet, its effect would be to stretch the pulses at the output (PROG OUT). Accordingly, when flip-flop U1-B is clocked, one side of the reed switch S1 is pulled to $V_B$ by the Q bar output of flip-flop U1-B. Diode CR4 is then back biased and reed switch S1 will not load down the PROG OUT pulse. This effectively disconnects the reed switch S1 from the circuit. Diode CR5 eliminates loading by the Q output of flip-flop U1-A which would be at $V_B$ when the flip-flop is reset. The PROG OUT output of FIG. 1 corresponds for example, to the data input of FIG. 3 of the above referenced copending Ser. No. 195,665 by analogy.

In the quiescent state, transistors Q1,Q2 and Q3 are off, dual flip-flop U1 is reset, reed switch S1 is open and PROG OUT is at $V_B$ by virtue of resistor R6. In this condition, the circuit of FIG. 1 is ready to receive incoming programming data via the tuned coil L1 or constant magnetic flux to actuate the reed switch S1 for the diagnostic mode. The diode logic arrangement of FIG. 1 ensures that programming and diagnostic modes have mutually exclusive sensors.

The following table lists typical component values for the correspondingly designated elements of FIG. 1 by way of illustration only. Actual values for other versions of the same circuit will vary depending on the application. For example, the resonant frequency of the tuned coil in the preferred embodiment is 16 KHz and the incoming magnetic pulse widths are on the order of 1 millisecond.

TABLE

| | |
|---|---|
| R1 | 100 kilohms |
| R2 | 100 kilohms |
| R3 | 1.5 megohms |
| R4 | 1.2 megohms |
| R5 | 8 megohms (active trim) |
| R6 | 1 megohm |
| C1 | .015 microfarad |
| C2 | 390 picofarads |
| C3 | .01 microfarad |
| L1 | 3.89 millihenries |
| Q3 | 2N2605 |
| U1 | CD4013 |

The advantage of using an electronic circuit in place of the reed switch for programming data is that it greatly expands the operating range without distortion of the duty cycle. Because the function of the reed switch itself is restricted to the diagnostic mode, the performance specifications for the reed switch are minimized so that a smaller reed switch can be used. In addition, because of the OR gate configuration of the programming output to the programming circuitry of the implant, the reed switch may still be used for programming if the tuned coil transponder circuit becomes nonfunctional for any reason. This redundancy in programming data input gives the pacer an extra margin of safety.

The above described circuitry can be varied and modified in many respects without departing from the underlying principle of the invention. For example, the reed switch S1 and associated circuitry may be omitted without affecting the reception of programming data. In fact, the diagnostic mode can be accessed by programming if desired. The circuit of FIG. 1 is also usable in connection with non-telemetry pacers, in which case the transistors Q1 and Q2 would not be present. In this form, the circuit could be operated using standard Cordis Omnicor programmer such as the Model 222. For example, in cardiac pacers which are programmed by counting the number of pulses received, pulse width is less critical and an analog pulse forming circuit, for example, a low current operational amplifier can be used in place of the flip-flop arrangement of FIG. 1 if desired.

The foregoing description is intended to be illustrative rather than restrictive, the scope of the invention being indicated by the appended claims.

What is claimed is:

1. In a programming system for a biomedical implant of the type wherein an external programmer produces a series of magnetic impulses which are received and transduced to form a corresponding electrical pulse input to programmable parameter data registers inside the implant, wherein the improvement comprises
   external programming pulse receiving and transducing circuitry in the implant including
   a tuned coil,
   means responsive to pairs of successive voltage spikes of opposite polarity magnetically induced across said tuned coil by said magnetic impulses for forming corresponding binary pulses duplicating said externally generated magnetic impulses giving rise to said spikes, and
   means for outputting said binary pulses to said data registers to accomplish programming of the implant.

2. The system of claim 1, wherein said tuned coil has a resonant frequency in the myriametric frequency range.

3. The sytem of claim 2, wherein said tuned coil has a resonant frequency of about 16 KHz.

4. The system of claim 1, wherein said pulse forming means includes means for producing a corresponding clock pulse with the occurrence of each said spike of either polarity, and
   flip-flop means responsive to said clock pulses for producing a binary data output corresponding to said magnetic impulses.

5. The system of claim 4, further comprising
   means for resetting said flip-flop means after a predetermined time interval.

6. The system of claim 1, further comprising
   a reed switch connected in parallel with the output of said outputting means, and
   means for isolating said reed switch when said pulse forming means is generating an output pulse.

7. The system of claim 4, further comprising
   a programming output terminal,
   a reed switch,
   respective diode means connecting the output of said one flip-flop means and one side of said reed switch, and
   means for grounding the other side of said reed switch whenever a succession of clock pulses is being received by said flip-flop means.

8. The system of claim 7, further comprising another flip-flop means having a clock input responsive to said clock pulses and a data input connected to a source of logically "high" voltage, the reset inputs to both said flip-flops being connected via an RC circuit to the Q output of said other flip-flop means and the other side of said reed switch being connected to the Q bar output of said other flip-flop means.

9. In a programming and telemetry system for a biomedical implant of the type wherein an external programmer produces a series of magnetic impulses which are received and transduced in the implant to form a corresponding electrical pulse input to programmable parameter data registers in the implant and an internal transmitter inside the implant transmits a digital information signal produced by the implant which is picked up by an external receiver, wherein the improvement comprises
   a tuned coil in the implant,
   a low impedance shunt circuit in the implant connected across said tuned coil including semiconductor means for modulating the impedance of said shunt circuit in accordance with said digital information signal to alter the phase and amplitude of a signal reradiated by said tuned coil in the presence of an externally generated magnetic carrier signal at the frequency to which said coil is tuned,
   means responsive to pairs of successive voltage spikes of opposite polarity magnetically induced across said tuned coil by said magnetic impulses for forming corresponding binary pulses duplicating said externally generated magnetic impulses giving rise to said spikes, and
   means for outputting said binary pulses to said data registers to accomplish programming of the implant.

10. The system of claim 9, wherein the frequency to which said coil is tuned is in the upper audio band.

11. The system of claim 10, wherein said semiconductor means includes a pair of series opposed transistors having respective gate terminals operatively connected to be driven by a digital information signal.

12. The system of claim 11, wherein said semiconductor means further includes a pair of series opposed diodes connected across the other two terminals of the respective ones of said transistors.

13. The system of claim 10, wherein the frequency to which said coil is tuned is about 16 KHz.

14. In a programming and telemetry system for a biomedical implant of the type wherein an external programmer produces a series of magnetic impulses which are received and transduced in the implant to form a corresponding electrical pulse input to programmable parameter data registers in the implant and an internal transmitter inside the implant transmits a digital information signal produced by the implant which is picked up by an external receiver, wherein the improvement comprises
   an external programmer including means for transmitting a carrier signal,
   a transceiver in the implant including a tuned coil for resonating at the frequency of said carrier signal so as to reradiate a signal at the frequency of said carrier signal and means for superimposing said digital information signal on the reflected signal,
   said programmer further including pick-up means for receiving the reflected signal from said transponder and means for recovering the information signal superimposed therein,
   said programmer further including an electromagnetic coil for producing said magnetic impulses,
   said implantable transceiver further including means responsive to pairs of successive voltage spikes of opposite polarity magnetically induced across said tuned coil by said magnetic impulses for forming corresponding binary pulses duplicating the externally generated magnetic impulses giving rise to said spikes, and means for outputting said binary pulses to said data registers to accomplish programming of the implant.

15. The system of claim 14, wherein said carrier signal and coil are tuned to the same frequency.

16. The system of claim 15, wherein said carrier signal and coil are tuned to a frequency in the upper audio band.

17. The system of claim 16, wherein said carrier signal and coil are tuned to a frequency of about 16 KHz.

* * * * *